United States Patent
Kim et al.

(10) Patent No.: US 11,484,562 B2
(45) Date of Patent: Nov. 1, 2022

(54) COMPOSITION FOR PREVENTING OR TREATING OBESITY COMPRISING NATURAL MIXTURE EXTRACTS

(71) Applicant: KOREA INSTITUTE OF ORIENTAL MEDICINE, Daejeon (KR)

(72) Inventors: Jin Sook Kim, Seoul (KR); Chan-Sik Kim, Sejong (KR); Ik Soo Lee, Daejeon (KR); Gyu Hyung Jo, Daejeon (KR); Soo-Wang Hyun, Gyeonggi-do (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 17/040,447

(22) PCT Filed: Dec. 11, 2018

(86) PCT No.: PCT/KR2018/015686
§ 371 (c)(1),
(2) Date: Dec. 18, 2020

(87) PCT Pub. No.: WO2019/182227
PCT Pub. Date: Sep. 26, 2019

(65) Prior Publication Data
US 2021/0113643 A1 Apr. 22, 2021

(30) Foreign Application Priority Data
Mar. 23, 2018 (KR) .................. 10-2018-0033922
Nov. 23, 2018 (KR) .................. 10-2018-0146737

(51) Int. Cl.
A61K 36/65 (2006.01)
A23L 33/00 (2016.01)
A23L 33/105 (2016.01)
A61P 3/04 (2006.01)
A61K 36/54 (2006.01)

(52) U.S. Cl.
CPC ............ *A61K 36/65* (2013.01); *A23L 33/105* (2016.08); *A23L 33/30* (2016.08); *A61K 36/54* (2013.01); *A61P 3/04* (2018.01); *A23V 2002/00* (2013.01); *A61K 2236/31* (2013.01); *A61K 2236/331* (2013.01); *A61K 2236/333* (2013.01); *A61K 2236/37* (2013.01)

(58) Field of Classification Search
None
See application file for complete search history.

(56) References Cited

U.S. PATENT DOCUMENTS

2017/0080043 A1* 3/2017 Zhou ................ A61P 19/06

FOREIGN PATENT DOCUMENTS

| CN | 1176814 | 3/1998 | |
|---|---|---|---|
| JP | H092966 | 1/1997 | |
| KR | 1019990011833 | 2/1999 | |
| KR | 1020090109446 | 10/2009 | |
| KR | 102010138118 | 12/2010 | |
| KR | 101289018 | 7/2013 | |
| KR | 102015135138 | 12/2015 | |
| WO | WO-2015172273 A1 * | 11/2015 | ........... A61K 36/484 |

OTHER PUBLICATIONS

Lin (Evidence-Based Complementary and Alternative Medicine (2013), article No. 207279, 8 pages).*
English translation of Chatani (JP H09002966 A) 1997.*
Han et al., "The extract of Cinnamomum cassia twigs inhibits adipocyte differentiation via activation of the insulin signaling pathway in 3T3-L1 preadipocytes" *Pharmaceutical Biology* 2013, 51(8), 961-967.
International Search Report and Written Opinion issued in Corresponding PCT Application No. PCT/KR2018/015686, dated Mar. 18, 2019 (English Translation provided).
Nagasawa, H et al., "Protection by tree-peony (*Paeonia suffruticosa* Andr) of obesity in (SLN x C3H/He) F1 obese mice." *In Vivo*. 1991, vol. 5, No. 2, pp. 115-118. (English Abstract).
Office Action issued in Corresponding Chinese Application No. 201880093681.7, dated Oct. 9, 2021 (No English Translation provided).
Shi Jinmo paired drugs. 4$^{th}$ ed., Jingshan Lv etc., 2015, p. 260 (English Abstract provided).
*Treatment of Obesity with Traditional Chinese Medicine*. 1$^{st}$ ed., Guangji Zhang etc., 2010, p. 165 (English Abstract provided).

* cited by examiner

*Primary Examiner* — Susan Hoffman
(74) *Attorney, Agent, or Firm* — Norton Rose Fulbright US LLP

(57) ABSTRACT

Provided is a composition for preventing or treating obesity including a mixed extract of Cinnamomi twigs, and more particularly, a pharmaceutical composition for preventing or treating obesity including a mixed extract of Cinnamomi twigs and Moutan root bark, a health functional food composition of feed composition for preventing or alleviating obesity including the composition, and a method of preventing or treating obesity including administering the pharmaceutical composition to an individual having obesity or a risk of developing obesity. The mixed extract of Cinnamomi twigs and Moutan root bark may inhibit fat absorption in the intestinal tract and increases in body weight causing obesity by single-dose administration, reduce lipid content in the blood, decrease weight and size of adipocytes, effectively inhibit accumulation of fat in liver tissue, and inhibit diarrhea, a serious side effect of Xenical™, by long-term administration.

3 Claims, 9 Drawing Sheets

[FIG. 1]
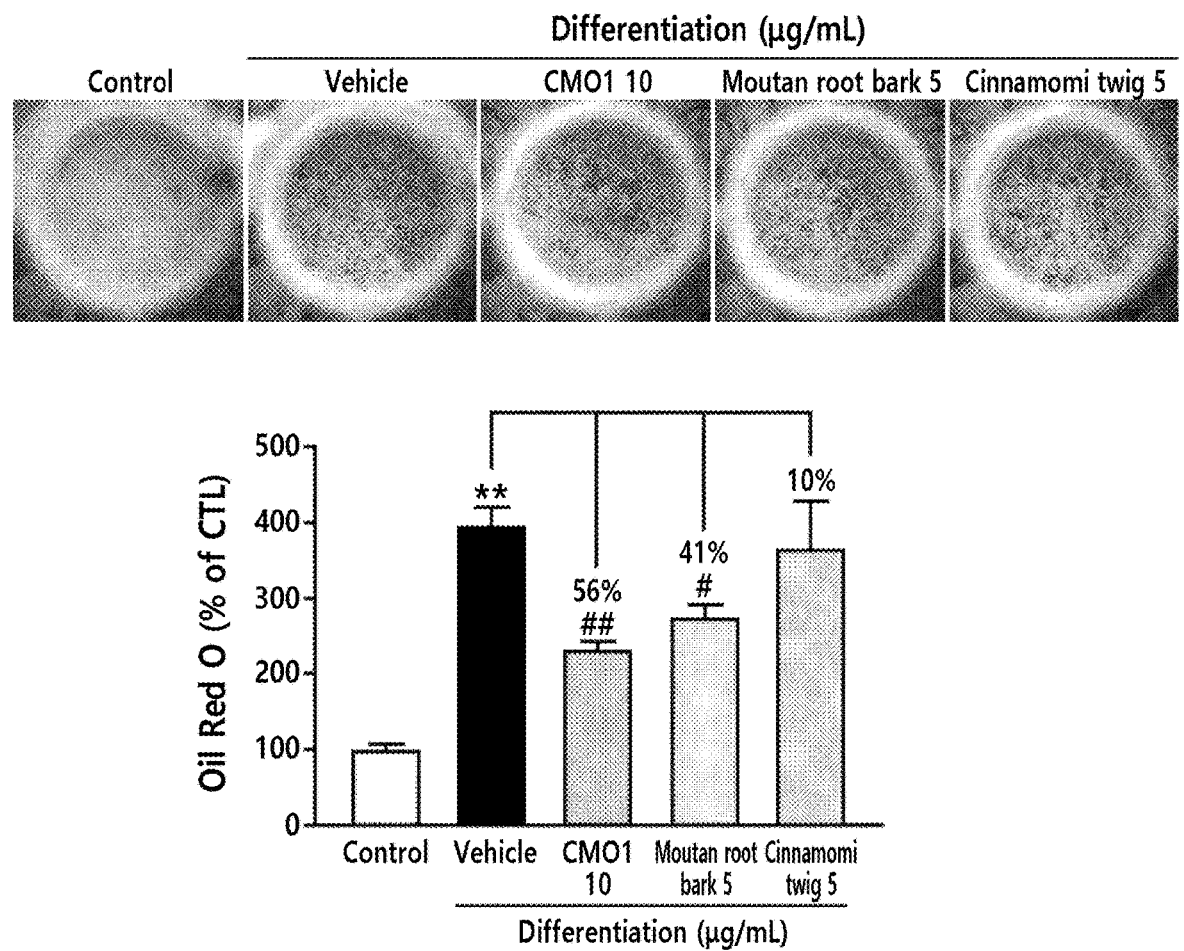

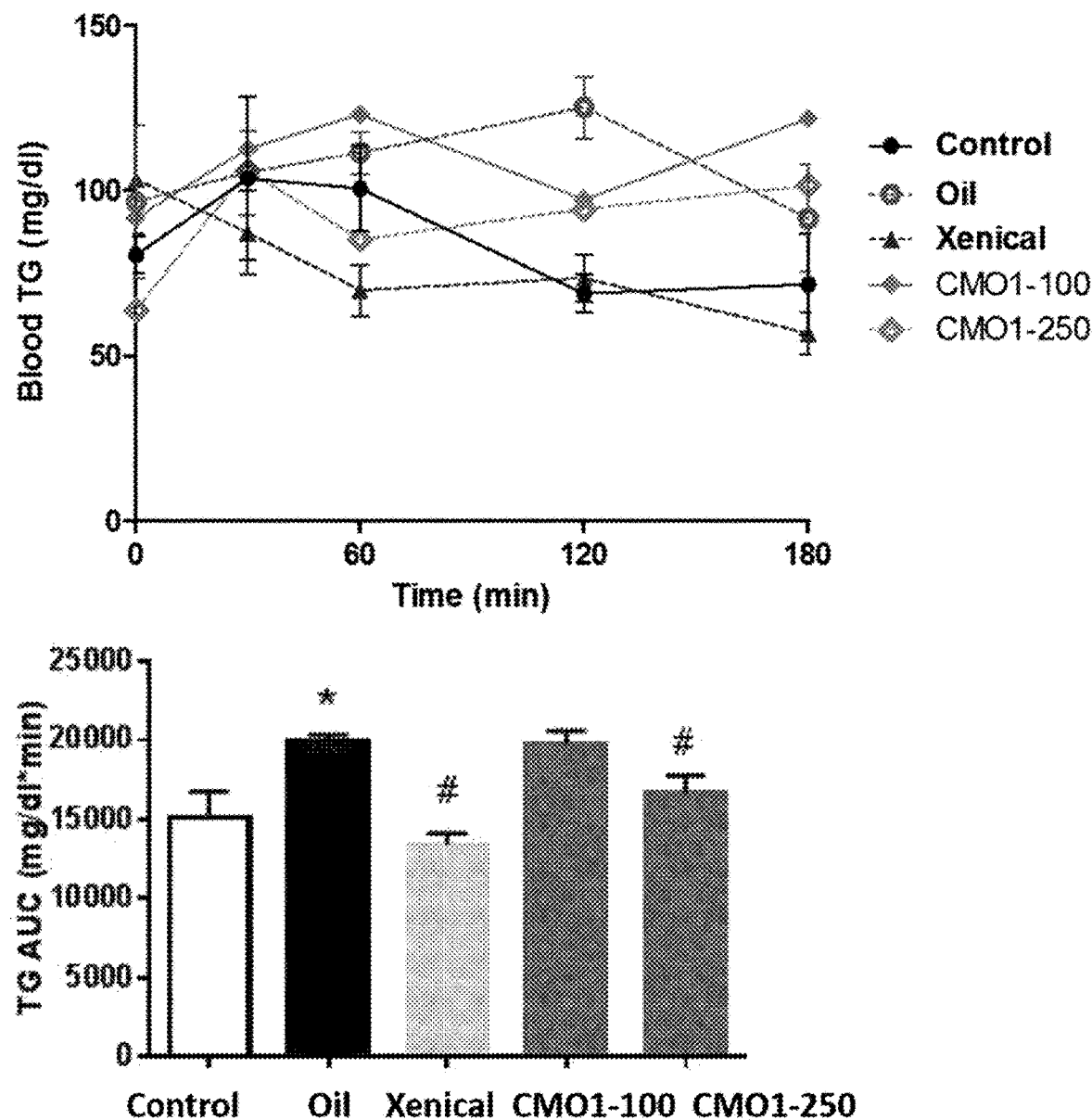
[FIG. 2]

[FIG. 3]
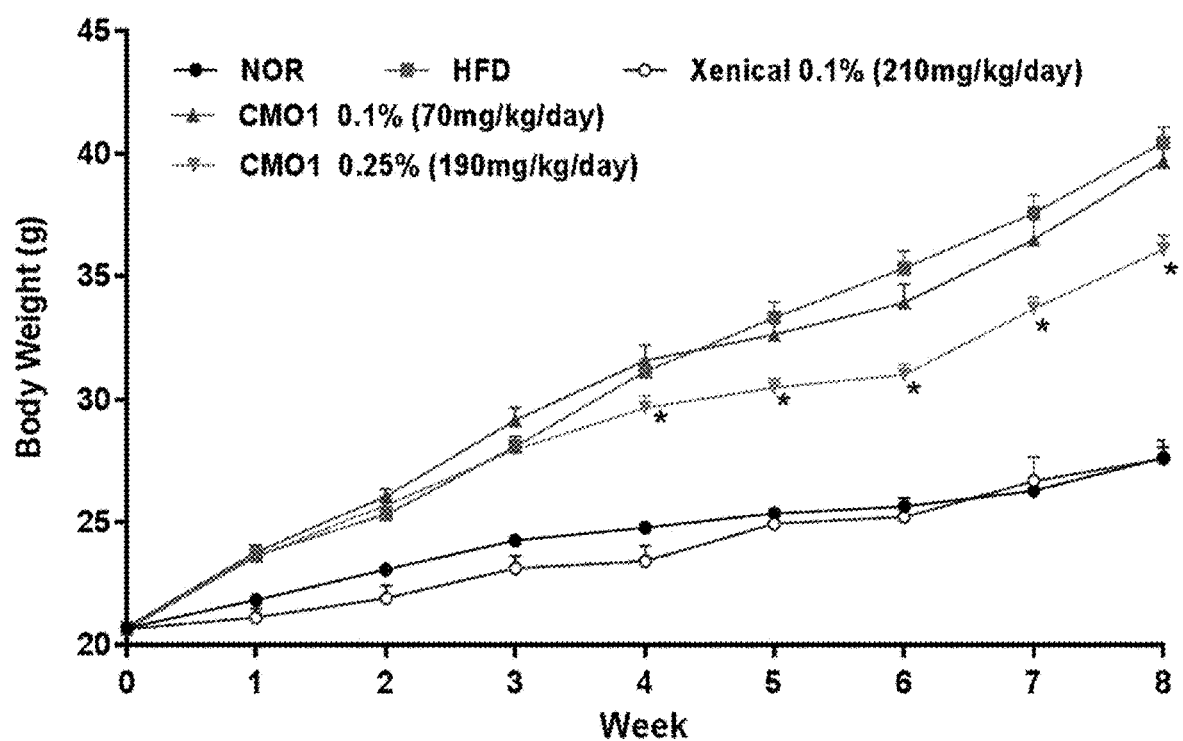

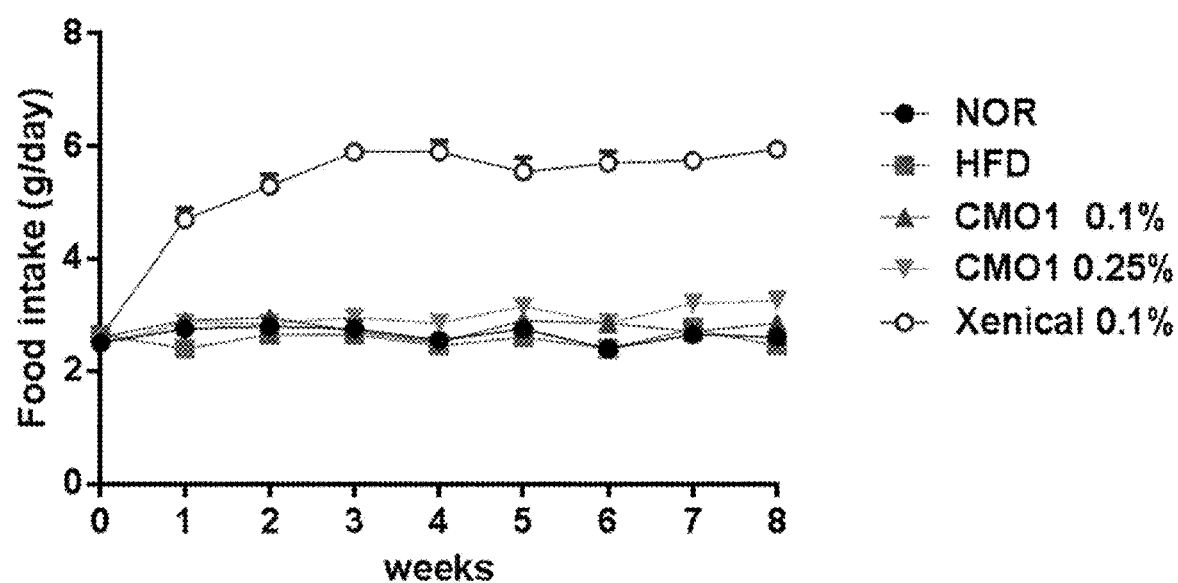
[FIG. 4]

[FIG. 5]
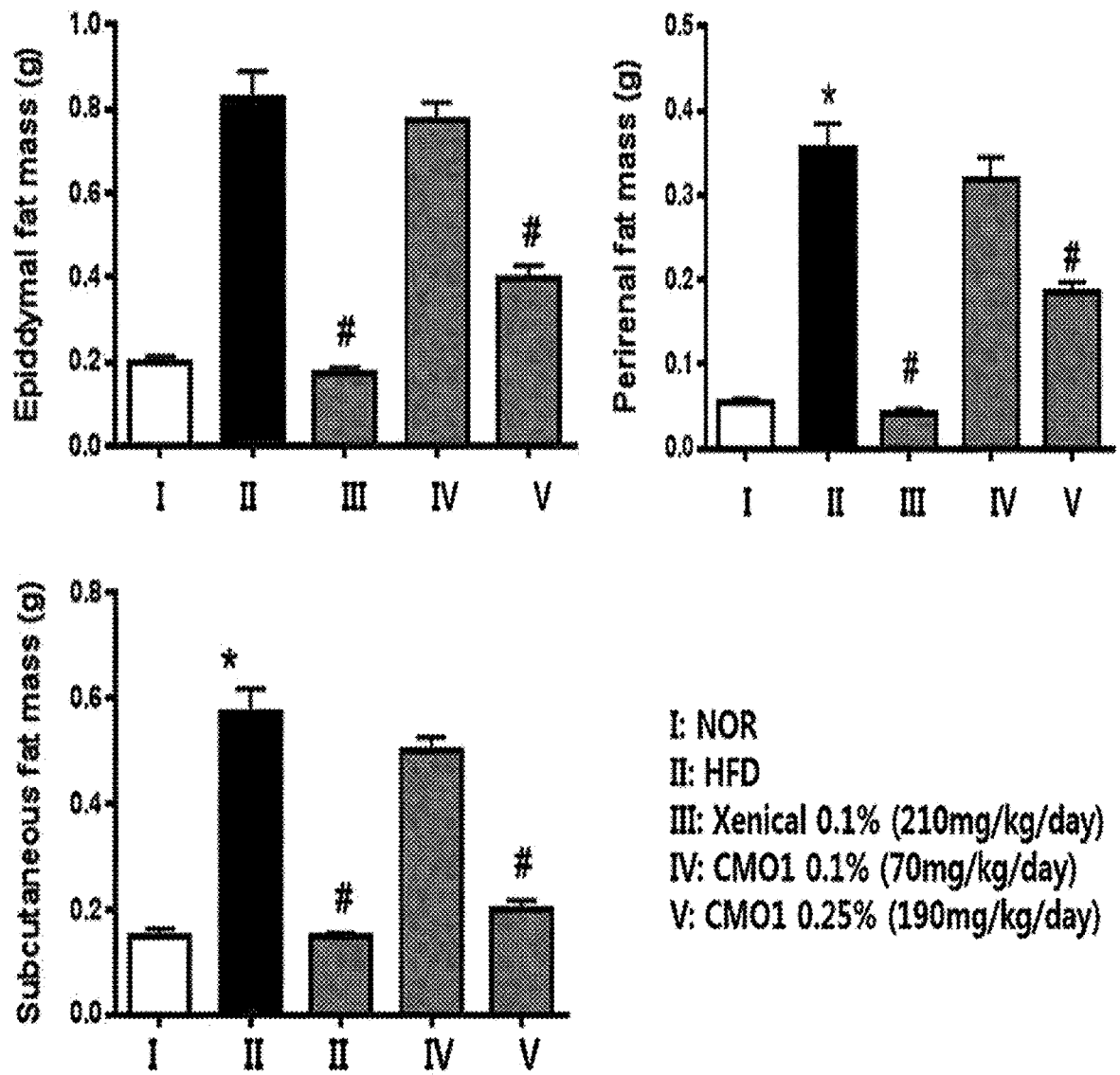

[FIG. 6]
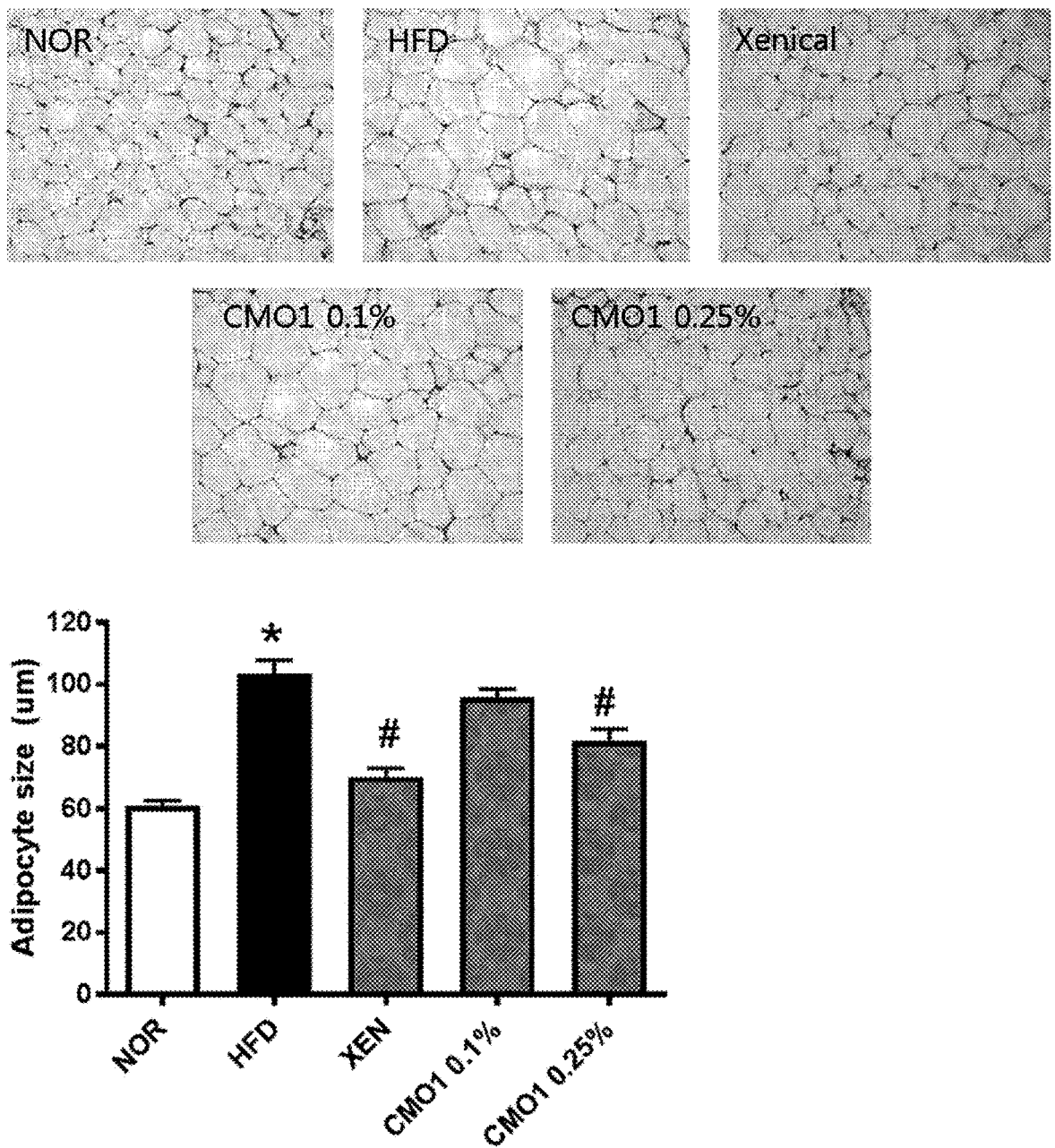

[FIG. 7]
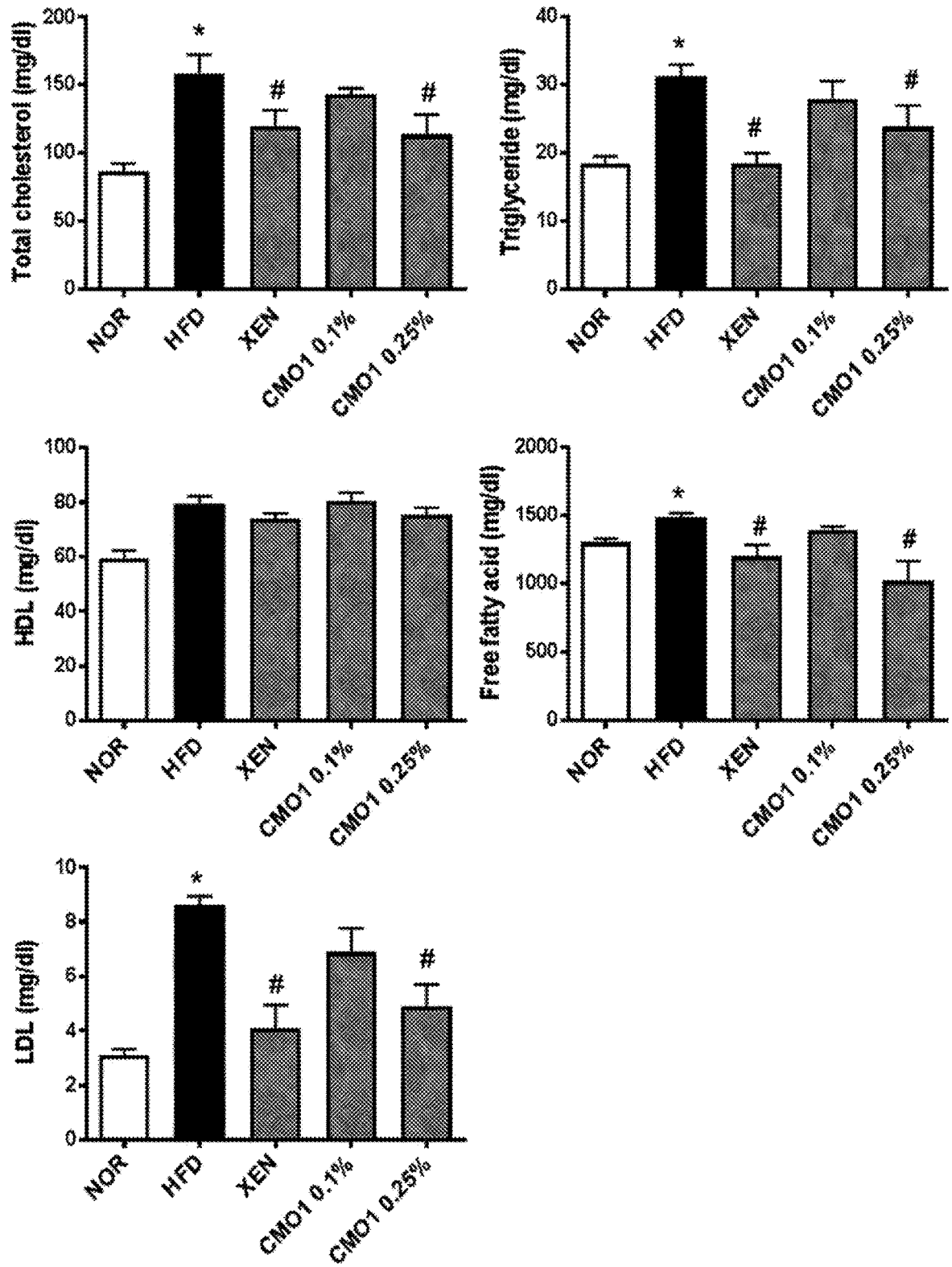

[FIG. 8]
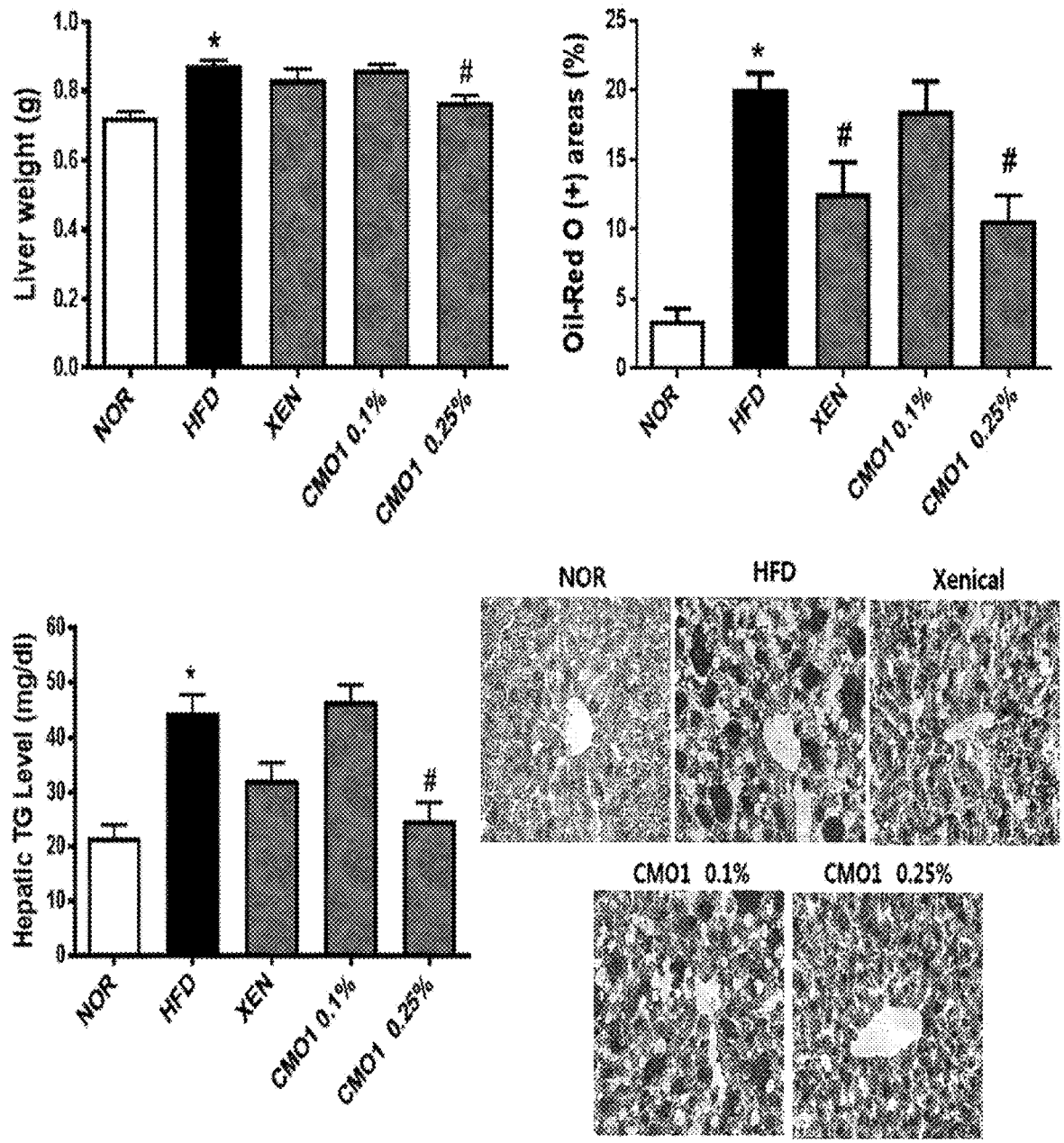

[FIG. 9]
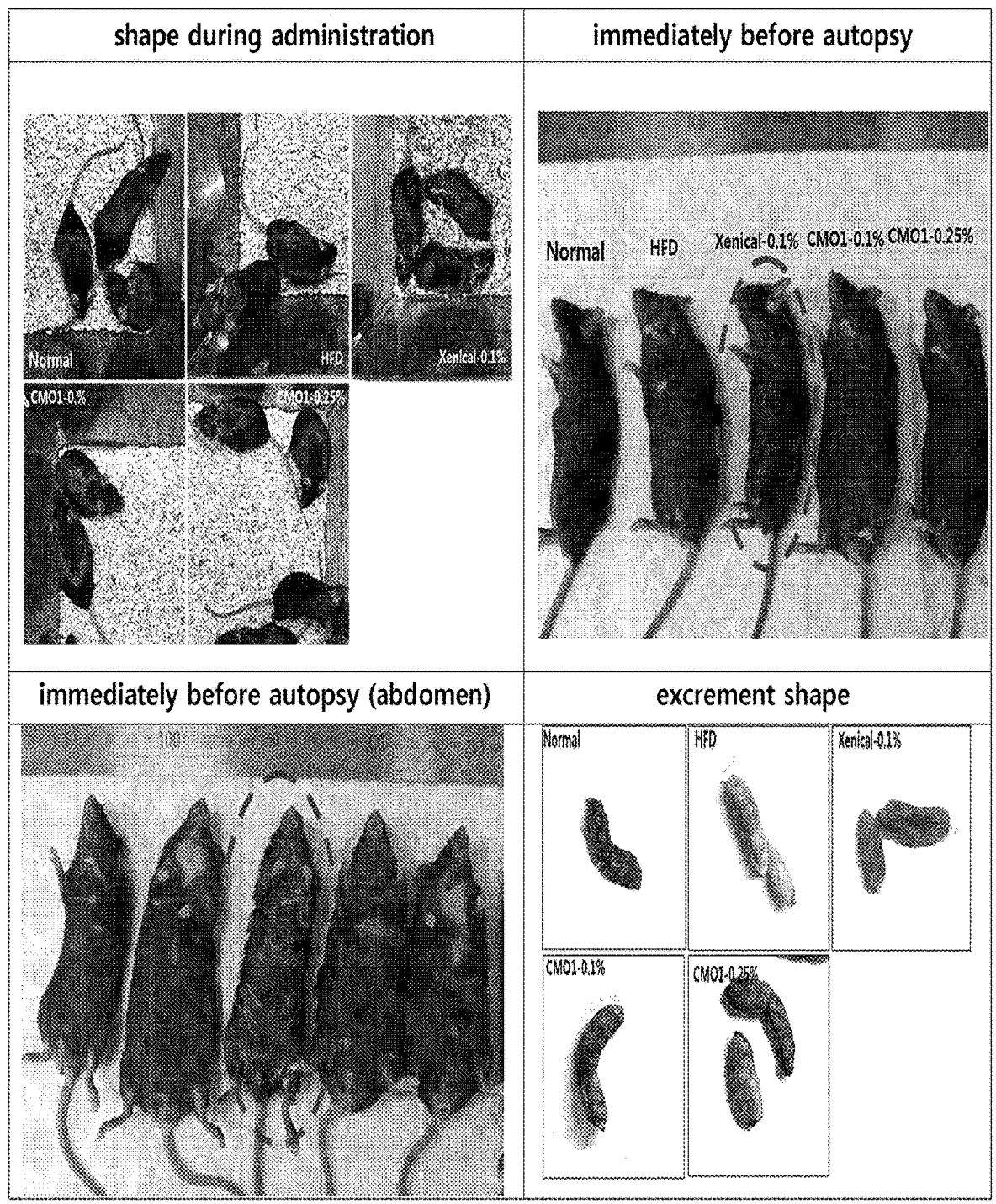

COMPOSITION FOR PREVENTING OR TREATING OBESITY COMPRISING NATURAL MIXTURE EXTRACTS

CROSS REFERENCE TO RELATED APPLICATIONS

This application is a national phase application under 35 U.S.C. § 371 of International Application No. PCT/KR2018/015686 filed Dec. 11, 2018, which claims the benefit of priority to Republic of Korea Patent Application Nos. 10-2018-0033922 filed Mar. 23, 2018 and 10-2018-0146737 filed Nov. 23, 2018.

FIELD OF THE INVENTION

The present invention relates to a composition for preventing or treating obesity including a mixed extract of Cinnamomi twigs, and more particularly, to a pharmaceutical composition for preventing or treating obesity including a mixed extract of Cinnamomi twigs and Moutan root bark, a health functional food composition and a feed composition for preventing or alleviating obesity including a mixed extract of Cinnamomi twigs and Moutan root bark, and a method of preventing or treating obesity including administering the pharmaceutical composition to an individual.

DESCRIPTION OF RELATED ART

With the development various technologies in modern society, humans enjoy affluent and comfortable living conditions. As a result, physical activity has decreased, and thus calorie expenditure has become less than calorie intake. Therefore, diseases such as overweight and obesity are increasing worldwide. According to the World Health Organization (WHO), about 1.6 billion people are obese or overweight worldwide at present, and the obese population is expected to continuously increase. Also, in Korea, the obese population has tended to rapidly increase due to westernized diet and lack of physical activity. A male adult obesity rate of 37.6% and female adult obesity rate of 28.0% were reported in Korea in 2013, and these numbers are expected to increase in the future. Since obesity may increase the incidence of complications such as cardiovascular disease, hyperlipidemia, decreased liver function, diabetes, endocrine disorders, lung dysfunction, and various cancers, the WHO has designated obesity as a major health issue rather than a simple cosmetic problem (in 2000).

Obesity results from an imbalance between energy intake and energy expenditure, and extensive research has been conducted worldwide into methods of preventing or treating obesity by inhibiting lipase, an enzyme that stores energy surplus in lipocytes to increase the number and size of the lipocytes.

As a representative example of therapeutic agents for obesity, Xenical™ (Orlistat) is a pancreatic lipase inhibitor with excellent efficacy of inhibiting absorption of approximately 30% of dietary fat, and the safety thereof has been approved as a drug for long-term administration (FDA, US). Although Xenical™ is the top-selling pharmaceutical product in the world, the effects thereof are not superior to those of an experimental group, in which obesity was treated only with diet, in the clinical trials (long-term administration for two years), and side effects such as facial paralysis, gastric disturbance, hypersensitivity, obstructed secretion of bile, and inhibition of fat-soluble vitamin absorption were confirmed. In particular, serious discomfort in daily life caused by diarrhea, constipation, indigestion, and the like have been proved. Reductil™ (Sibutramine) has been withdrawn from the market since cardiovascular side effects have been confirmed. A higher number of cardiovascular events have been observed in people taking Reductil™ verses a control group by 16%. Approval of Acomplia™ (Rimonabat) by the European Union (EU) was revoked due to psychiatric side effects such as depression. It has been reported that Contrave™ (Naltrexone/bupropion) may affect suicidal impulse and suicidality.

As described above, therapeutic agents for obesity currently on the market have serious problems, and thus there is an urgent need to develop therapeutic agents therefor with improved efficacy without side effects. As a method to overcome these problems, development of therapeutic agents using natural substances, the safety of which has been proved, has attracted much attention. Extensive research has been conducted into therapeutic agents for obesity and health functional foods for preventing or alleviating obesity using natural substances.

Meanwhile, a Cinnamomi twig is a young branch of *Cassia* bark tree (or Cinnamon tree), which is a tall evergreen tree of the genus *Cinnamomum* in the Lauraceae family, and has spicy and sweet tastes and warm properties affecting the heart, lung, and bladder. Cinnamomi twigs are known to strengthen the stomach, inhibit stroke, have pain-relief and cardiotonic actions, expand cutaneous blood vessels, stimulate sweat glands to induce perspiration resulting in antipyretic action, and have anti-virus action. Cinnamomi twigs are also used to treat chills, fever, headaches, body aches, lack of perspiration, and palpitations. Cinnamomi twigs have a long cylindrical shape with many branches and have a length of 30 cm to 70 cm and a diameter in thicker parts of 0.3 cm to 1 cm. The surface has vertical ridgelines in a reddish-brown or brown color, and has traces of leaves and branches in the form of thin wrinkles and small lumps. Cinnamomi twigs with hard, fragile, and easy-to-cut properties are mainly produced in Guangxi and Guangdong Province of China, and are also cultivated in Vietnam, Sri Lanka, and India. As a result of pharmacological experiments on Cinnamomi twigs, perspiratory, antipyretic, pain-relief, cardiotonic, anti-allergic, and anti-viral actions thereof have been revealed.

Moutan root bark is used as an antiphlogistic coagulant treating blood extravasation for oriental medicine due to its cold property. Medicinal effects thereof on inflammation in vascular systems of lower abdominal organs, pains due to congestion, fever, suppuration, bleeding, and the like, particularly, anti-inflammation, contraction, spasmolysis for menstrual irregularity, inflammation in the uterus and adnexa, congestion, and dragging pain have been known, and Moutan root bark is also applied to treat hemorrhoids and epityphlitis.

SUMMARY OF THE INVENTION

Therefore, the present inventors have confirmed that a mixed extract of Cinnamomi twigs and Moutan root bark may treat overweight and obesity via inhibition of fat absorption, and the mixed extract has no side effects of diarrhea caused by conventional therapeutic agents, thereby completing the present invention.

An object of the present invention is to provide a pharmaceutical composition for preventing or treating obesity including a mixed extract of Cinnamomi twigs and Moutan root bark.

Another object of the present invention is to provide a use of a mixed extract of Cinnamomi twigs and Moutan root bark for preventing or treating obesity.

Another object of the present invention is to provide a health functional food composition for preventing or alleviating obesity including a mixed extract of Cinnamomi twigs and Moutan root bark.

Another object of the present invention is to provide a feed composition for preventing or alleviating obesity including a mixed extract of Cinnamomi twigs and Moutan root bark.

Another object of the present invention is to provide a method of preventing or treating obesity including administering a mixed extract of Cinnamomi twigs and Moutan root bark to an individual.

The mixed extract of Cinnamomi twigs and Moutan root bark of the present invention may inhibit in vivo fat absorption and size increases of adipocytes closely related to obesity, inhibit or treat abnormal increases in related factors such as cholesterols and triglycerides, and inhibit diarrhea, which is a serious side effect of conventional therapeutic agents. Therefore, the mixed extract may be widely used in development of pharmaceutical compositions for preventing or treating obesity.

BRIEF DESCRIPTION OF DRAWINGS

FIG. 1 is a graph illustrating adipocyte differentiation inhibitory effects of a mixed extract of Cinnamomi twigs and Moutan root bark (CMO1), a Moutan root bark extract, a Cinnamomi twig extract in adipocyte cell lines (3T3L1) (**$P<0.01$ vs. control, ##$P<0.01$ vs. vehicle, #$P<0.05$ vs. vehicle).

FIG. 2 is a graph illustrating in vivo fat absorption inhibitory effects of the mixed extract of Cinnamomi twigs and Moutan root bark (CMO1) (Mean±SEM. *$p<0.05$ vs. control, #$p<0.05$ vs. oil emulsion).

FIG. 3 is a graph illustrating changes in body weights of the mixed extract of Cinnamomi twigs and Moutan root bark (CMO1) in high-fat diet-fed mice (NOR: normal-fat diet-fed group, HFD: high-fat diet-fed group, CMO1-0.1%: HFD plus 0.1% CMO1 (w/w; 70 mg/kg/day), CMO1-0.25%: HFD plus 0.25% CMO1 (w/w; 190 mg/kg/day), Xenical-0.1%: HFD plus 0.1% Xenical (w/w; 210 mg/kg/day). Means±SEM. *$p<0.05$ vs. HFD group).

FIG. 4 is a graph illustrating effects of the mixed extract of Cinnamomi twigs and Moutan root bark (CMO1) on daily food intakes in high-fat diet-fed mice (NOR: normal-fat diet-fed group, HFD: high-fat diet-fed group, CMO1-0.1%: HFD plus 0.1% CMO1 (w/w; 70 mg/kg/day), CMO1-0.25%: HFD plus 0.25% CMO1 (w/w; 190 mg/kg/day), Xenical-0.1%: HFD plus 0.1% Xenical (w/w; 210 mg/kg/day)).

FIG. 5 is a graph illustrating effects of the mixed extract of Cinnamomi twigs and Moutan root bark (CMO1) on body fat weights in high-fat diet-fed mice (NOR: normal-fat diet-fed group, HFD: body fat weight, CMO1-0.1%: HFD plus 0.1% CMO1 (w/w; 70 mg/kg/day), CMO1-0.25%: HFD plus 0.25% CMO1 (w/w; 190 mg/kg/day), Xenical-0.1%: HFD plus 0.1% Xenical (w/w; 210 mg/kg/day). Means±SEM, *$p<0.05$ vs. NOR group, #$p<0.05$ vs. HFD group).

FIG. 6 shows paraffin sections of adipocytes stained with hematoxylin and eosin illustrating morphologies of white adipose tissue and sizes of the adipocytes (NOR: normal-fat diet-fed group, HFD: high-fat diet-fed group, CMO1-0.1%: HFD plus 0.1% CMO1 (w/w; 70 mg/kg/day), CMO1-0.25%: HFD plus 0.25% CMO1 (w/w; 190 mg/kg/day), Xenical-0.1%: HFD plus 0.1% Xenical (w/w; 210 mg/kg/day). Means±SEM, *$p<0.05$ vs. NOR group, #$p<0.05$ vs. HFD group).

FIG. 7 show graphs illustrating effects of the mixed extract of Cinnamomi twigs and Moutan root bark (CMO1) on lipid content in the blood (NOR: normal-fat diet-fed group. HFD: high-fat diet-fed group, CMO1-0.1%: HFD plus 0.1% CMO1 (w/w; 70 mg/kg/day), CMO1-0.25%: HFD plus 0.25% CMO1 (w/w; 190 mg/kg/day), Xenical-0.1%: HFD plus 0.1% Xenical (w/w; 210 mg/kg/day). Means±SEM, *$p<0.05$ vs. NOR group, #$p<0.05$ vs. HFD group).

FIG. 8 shows effects of the mixed extract of Cinnamomi twigs and Moutan root bark (CMO1) on fatty liver in high-fat diet-fed mice. In hepatocytes, fats were identified by Oil red O staining (HFD: high-fat diet-fed group, CMO1-0.1%: HFD plus 0.1% CMO1 (w/w; 70 mg/kg/day), CMO1-0.25%: HFD plus 0.25% CMO1 (w/w; 190 mg/kg/day), Xenical-0.1%: HFD plus 0.1% Xenical (w/w; 210 mg/kg/day). Means±SEM, *$P<0.05$ vs. NOR group, #$p<0.05$ vs. HFD group).

FIG. 9 is a view for verifying presence of diarrhea, which is a serious side effect of Xenical™.

As a result of intensive efforts to develop therapeutic agents for the effective treatment of obesity, the present inventors have found that a mixed extract of Cinnamomi twigs, specifically, a mixed extract of Cinnamomi twigs and Moutan root bark, has therapeutic effects on obesity. Specifically, it was confirmed that the mixed extract of Cinnamomi twigs and Moutan root bark significantly inhibits in vivo fat absorption, indicating preventive or therapeutic effects on obesity, and has no side effects of conventional therapeutic agents.

An aspect of the present invention to achieve the above-described objects provides a pharmaceutical composition for preventing or treating obesity including a mixed extract of Cinnamomi twigs and Moutan root bark.

In addition, another aspect of the present invention provides a use of the mixed extract of Cinnamomi twigs and Moutan root bark for preventing or treating obesity.

As used herein, the term "Cinnamomi twig" refers to a young branch of a *Cassia* bark tree (Cinnamon tree), which is a tall evergreen tree of the genus *Cinnamomum*, and which has spicy and sweet tastes and warm properties affecting the heart, lung, and bladder. Cinnamomi twigs are known to strengthen the stomach, inhibit stroke, have pain-relief and cardiotonic actions, expand cutaneous blood vessels, stimulate sweat glands to induce perspiration resulting in antipyretic action, and anti-virus action. Cinnamomi twigs are also used to treat chills, fever, headaches, body aches, lack of perspiration, and palpitations. Cinnamomi twigs have a long cylindrical shape with many branches and have a length of 30 cm to 70 cm and a diameter of thicker parts of 0.3 cm to 1 cm. The surface has vertical ridgelines in a reddish-brown or brown color and has traces of leaves and branches in the form of thin wrinkles and small lumps. Cinnamomi twigs with hard, fragile, and easy-to-cut properties are mainly produced in Guangxi and Guangdong Province of China and are also cultivated in Vietnam, Sri Lanka, and India. As a result of pharmacological experiments on Cinnamomi twigs, perspiratory, antipyretic, pain-relief, cardiotonic, anti-allergic, and anti-virus actions thereof have been revealed.

As used herein, the term "Moutan root bark" is an important herbal medicine which has been used since long ago and is used as an antiphlogistic coagulant treating blood extravasation for oriental medicine due to its cold property. Medicinal effects thereof on inflammation in vascular systems of lower abdominal organs, pains due to congestion, fever, suppuration, bleeding, and the like, particularly, anti-inflammation, contraction, spasmolysis for menstrual irregularity, inflammation in the uterus and adnexa, congestion, and dragging pain have been known, and Moutan root bark is also applied to treat hemorrhoids and epityphlitis.

The Cinnamomi twigs and Moutan root bark may be harvested in the wild, farmed, or commercially purchased, without being limited thereto.

As used herein, the term "extract" refers to a substance obtained using at least one solvent, and examples of the solvent used to prepare the extract may include water, C1 to C4 alcohols, preferably, methanol, ethanol, butanol, and any mixed solvent thereof, without being limited thereto. As a method for extraction, high-temperature decompression extraction, hot-water extraction, reflux extraction, hydrothermal extraction, maceration extraction, room-temperature extraction, reflux cooling extraction, ultrasonication extraction, or steam extraction may be used, without being limited thereto.

The "mixed extract" may be prepared by extracting each of Cinnamomi twigs and Moutan root bark and then mixing the extracts, or may also be prepared by mixing Cinnamomi twigs and Moutan root bark and then extracting.

The Cinnamomi twigs and Moutan root bark may be mixed at a weight ratio of 1:1 to 1:10, specifically at a weight ratio of 1:1, 1:2, 1:4, 1:8, 2:1, 4:1, or 8:1, without being limited thereto.

As used herein, the term "obesity" refers to a health condition in which adipose tissue is excessive in the body. When a body mass index (a value obtained by dividing a person's body weight (kg) by the square of his/her height ($m^2$)) of a person is 25 or higher, the person is defined as being obese. Obesity is caused by energy imbalance when an energy intake exceeding energy expenditure continues for a long time and fatty acids and glucose introduced from plasma into adipocytes are esterified and accumulated mainly in the form of triglycerides.

As used herein, the term "prevention" refers to any action resulting in inhibition or delay of obesity by administering the composition including the mixed extract of Cinnamomi twigs and Moutan root bark according to the present invention.

As used herein, the term "treatment" refers to any action resulting in improvement or beneficial alternation of symptoms of obesity by administering the composition including the mixed extract of Cinnamomi twigs and Moutan root bark according to the present invention.

As used herein, the term "pharmaceutical composition" refers to a composition prepared for the purpose of preventing or treating a disease, and may be formulated in various forms according to methods commonly used in the art. For example, the pharmaceutical composition may be formulated into a powder, a granule, a tablet, a capsule, a suspension, an emulsion, or a syrup, and may also be formulated into a formulation for external use, a suppository, and a sterile injection solution. Specifically, the pharmaceutical composition may be formulated into a formulation suitable for administration to the eyes, e.g., an eye drop, a cream, an ointment, a gel, or a lotion.

The composition of the present invention may be formulated into a pharmaceutical composition for preventing or treating obesity including any carrier, excipient, or diluent which is commonly used in preparation of pharmaceutical compositions. The carrier may include a carrier which is not naturally occurring.

In the present invention, examples of the carrier, excipient, and diluent included in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methyl hydroxy benzoate, propyl hydroxy benzoate, talc, magnesium stearate, and mineral oil.

For formulation, a typically used diluent or excipient such as a filler, a thickener, a binder, a humectant, a disintegrant, a surfactant, or the like may be used. Solid formulations for oral administration may include tablets, pills, powders, granules, capsules, and the like. Such solid formulations may be prepared by mixing with at least one excipient, for example, starch, calcium carbonate, sucrose, lactose, or gelatin. In addition to simple excipients, lubricants such as magnesium stearate or talc may also be used. Liquid formulations for oral administration may be suspensions, formulations for internal use, emulsions, syrups, or the like, and may include various excipients such as humectants, sweeteners, fragrances, and preservatives in addition to simple diluents commonly used in the art such as water or liquid paraffin. Formulations for parenteral administration may include sterile aqueous solutions, non-aqueous solvents, suspensions, emulsions, lyophilizates, suppositories, and the like. The non-liquid solutions and suspensions may be propylene glycol, polyethylene glycol, vegetable oils such as olive oil, injectable esters such as ethyl oleate, or the like. Bases for the suppositories may include Witepsol, Macrogol, Tween 61, cacao butter, laurin butter, glycerogelatin, or the like.

Dosage of the pharmaceutical composition of the present invention may be determined by one of ordinary skill in the art according to the purpose of use, severity of disease, age, body weight, gender, or medical history of a patient, or type of a substance used as an active ingredient. For example, the pharmaceutical composition of the present invention may be administered in an amount of about 0.1 ng to about 1,000 mg/kg, specifically, about 1 ng to about 1,000 mg/kg per adult, and administration frequency may be, but is not particularly limited to, once a day or many times a day in divided doses. However, the scope of the present invention is not limited by the dosage in any manner.

In an embodiment of the present invention, when the mixed extract of Cinnamomi twigs and Moutan root bark was administered, it was confirmed that adipocyte differentiation inhibitory effects were improved (FIG. 1), the total amount of triglycerides was significantly reduced (FIG. 2), an increase in body weight was significantly inhibited (FIG. 3), changes in abdominal fat and fat weight were inhibited, and adipocyte hypertrophy caused by fat accumulation was inhibited (FIGS. 4 to 6), compared to when either the Cinnamomi twig extract or the Moutan root bark extract was administered. Also, when the mixed extract of Cinnamomi twigs and Moutan root bark was administered, it was confirmed that concentrations of total cholesterol, triglycerides, and LDL cholesterol, and free fatty acids were significantly reduced (FIG. 7), increased liver weight and the area of lipid in hepatocytes were significantly decreased, and the amount of triglycerides was significantly reduced in liver tissue (FIG. 8).

In particular, while the control drug Xenical™ has side effects of serious diarrhea, hair was normal and no frequent diarrhea was observed during administration of the mixed extract of Cinnamomi twigs and Moutan root bark to mice, indicating effects on overcoming the serious side effects of Xenical™ (FIG. 9).

Another aspect of the present invention provides a health functional food composition for preventing or alleviating obesity including a mixed extract of Cinnamomi twigs and Moutan root bark.

Also, another aspect of the present invention provides a food composition for preventing or alleviating obesity including a mixed extract of Cinnamomi twigs and Moutan root bark.

As used herein, the terms "Cinnamomi twigs", "Moutan root bark", "mix", "extract", "obesity", and "prevention" are as defined above.

The health functional food composition or food composition of the present invention may further include a sitologically acceptable carrier.

As used herein, the term "alleviation" refers to any action that ameliorates or beneficially changes obesity due to administration of the composition.

In addition, the alleviation may also mean allowing obese people to live ordinary lives by reducing and weakening side effects of the currently available therapeutic agents.

Examples of the food to which the composition including the mixed extract of the Cinnamomi twigs of the present invention is added are not particularly limited, but may be, for example, various beverages, gums, teas, vitamin complexes, and dietary supplements. The food composition may further include any other ingredient that does not inhibit therapeutic effects on obesity, and types thereof are not particularly limited. For example, the food composition, like other foods, may further include various herb extracts, sitologically acceptable food auxiliary additives, or natural carbohydrates.

The food auxiliary additive may be an additive used to prepare the food composition of each formulation, and may be appropriately selected by those of ordinary skill in the art. For example, various nutrients, vitamins, minerals, flavors such as synthetic and natural flavors, colorants and fillers, pectic acid and salts thereof, alginic acid and salts thereof, organic acids, protective colloidal thickeners, pH regulators, stabilizers, antiseptics, glycerin, alcohols, carbonating agents used in soda may be included, without being limited thereto.

The amount of the extract included in the food is not particularly limited but may be in the range of 0.01 wt % to 100 wt %, preferably 1 wt % to 80 wt %, based on a total weight of the food composition.

When the food is a beverage, the extract may be included therein in an amount of 1 g to 30 g, preferably 3 g to 20 g, based on 100 mL of the food. Also, the composition may further include an additional ingredient capable of improving smell, taste, appearance, and the like which is commonly used in food compositions. For example, the composition may include vitamin A, C, D, E, B1, B2, B6, or B12, niacin, biotin, folate, pantothenic acid, or the like. Also, the composition may include minerals such as zinc (Zn), iron (Fe), calcium (Ca), chromium (Cr), magnesium (Mg), manganese (Mn), or copper (Cu). Also, the composition may include amino acids such as lysine, tryptophan, cysteine, or valine. In addition, food additives such as antiseptics (potassium sorbate, sodium benzoate, salicylic acid, sodium dehydroacetate, or the like), disinfectants (bleaching powder, higher bleaching powder, sodium hypochlorite, or the like), antioxidants (butylhydroxyanisole (BHA), butylhydroxytoluene (BHT), or the like), colorants (tar color, or the like), color-developing agents (sodium nitrite), bleaching agents (sodium sulfite), seasonings (monosodium glutamate (MSG), or the like), sweeteners (dulcin, cyclemate, saccharin, sodium, or the like), flavors (vanillin, lactones, or the like), swelling agents (alum, potassium D-bitartrate, or the like), fortifiers, emulsifiers, thickeners (adhesive pastes), film-forming agents, gum base agents, antifoaming agents, solvents, and improvers may be added thereto. The additives may be selected and used in an appropriate amount according to types of the food.

The health functional food composition of the present invention may be prepared using a method commonly used in the art. Substances and ingredients commonly used in the art may be added thereto in preparation thereof. The health functional food composition may be prepared into any formulation that is regarded as a health functional food composition, without limitation. The health functional food composition of the present invention may be prepared into various formulations and has an advantage over general drugs in that the food composition is free of side effects which might occur upon long-term intake of drugs because it is based on food materials. Furthermore, the health functional food composition of the present invention is of high portability such that it may be ingested as a supplement for promoting the preventive or alleviative effect on obesity.

Another aspect of the present invention provides a feed composition for preventing or alleviating obesity including a mixed extract of Cinnamomi twigs and Moutan root bark.

As used herein, the terms "Cinnamomi twigs", "Moutan root bark", "mix", "extract", "obesity", and "prevention" are as defined above.

The feed composition may further include a carrier acceptable as feed.

Examples of the feed to which the composition including the mixed extract of the Cinnamomi twigs of the present invention is added are not particularly limited, but may be, for example, various beverages, gums, teas, vitamin complexes, and dietary supplements. The feed composition may further include any other ingredient that does not inhibit therapeutic effects on obesity, and types thereof are not particularly limited. For example, the feed composition, like other feeds, may further include various herb extracts, food, feed auxiliary additives acceptable for feeds, or natural carbohydrates.

The feed auxiliary additive may be an additive used to prepare a feed composition of each formulation and may be appropriately selected by those of ordinary skill in the art. For example, various nutrients, vitamins, minerals, flavors such as synthetic and natural flavors, colorants and fillers, pectic acid and salts thereof, alginic acid and salts thereof, organic acids, protective colloidal thickeners, pH regulators, stabilizers, antiseptics, glycerin, alcohols, carbonating agents used in soda may be included, without being limited thereto.

In this regard, the amount of the extract included in the feed is not particularly limited, but may be in the range of 0.01 wt % to 100 wt %, preferably 1 wt % to 80 wt %, based on a total weight of the feed composition.

Another aspect of the present invention provides a method of preventing or treating obesity including administering the pharmaceutical composition to an individual having obesity or at risk of developing obesity.

As used herein, the terms "Cinnamomi twig", "Moutan root bark", "mix", "extract", "obesity", and "treatment" are as defined above.

As used herein, the term "individual" refers to a mammal having obesity such as rats and livestock.

The composition may be administered in a single dosage or multiple dosages in a pharmaceutically effective amount.

The administration of the pharmaceutical composition for preventing or treating obesity of the present invention may be performed via any conventional route of administration to deliver the composition to a target tissue.

The pharmaceutical composition of the present invention may be administered according to a desired purpose via a route of administration such as eye-drop administration, intraperitoneal administration, intravenous administration, intramuscular administration, subcutaneous administration, intradermal administration, transdermal patch administration, oral administration, intranasal administration, intrapulmonary administration, and rectal administration, particularly, via oral administration, without being limited thereto.

EXAMPLES

Example 1. Preparation of Mixed Extract of Cinnamomi Twigs and Moutan Root Bark

Cinnamomi twigs and Moutan root bark were used for the following examples and kept in a cold room of the diabetic complications research team at the Korea Institute of Oriental Medicine.

1-1. Preparation of Extract of Cinnamomi Twigs and Moutan Root Bark (1:1) (CMO1)

An extract of Cinnamomi twigs and Moutan root bark (CMO1) was prepared by mixing 12 g of Cinnamomi twigs and 12 g of Moutan root bark at a ratio of 1:1, adding the mixture (24 g in total) to 144 mL of 50% ethanol, and repeatedly extracting the resultant twice under reflux at about 50° C. for about 3 hours.

1-2. Preparation of Hydrothermal Extract of Cinnamomi Twigs and Moutan Root Bark (1:1) (CMO1-1)

A hydrothermal extract of Cinnamomi twigs and Moutan root bark (CMO1-1) was prepared by mixing 90 g of Cinnamomi twigs and 90 g of Moutan root bark at a ratio of 1:1, adding the mixture (180 g in total) to 1080 mL of purified water, and extracting the resultant under hydrothermal conditions in an herbal-decoction machine for about 2 hours.

1-3. Preparation of Extract of Cinnamomi Twigs and Moutan Root Bark (1:2) (CMO2)

An extract of Cinnamomi twigs and Moutan root bark (CMO2) was prepared in the same manner as in Example 1-1, except that 10 g of Cinnamomi twigs and 20 g of Moutan root bark were mixed at a ratio of 1:2, the mixture (30 g in total) was added to 180 mL of 50% ethanol, and the resultant was repeatedly extracted twice under reflux at about 50° C. for about 3 hours.

1-4. Preparation of Hydrothermal Extract of Cinnamomi Twigs and Moutan Root Bark (1:2) (CMO2-1)

A hydrothermal extract of Cinnamomi twigs and Moutan root bark (CMO2-1) was prepared in the same manner as in Example 1-2, except that 60 g of Cinnamomi twigs and 120 g of Moutan root bark were mixed at a ratio of 1:1, the mixture (180 g in total) was added to 1080 mL of purified water, and the resultant was extracted under hydrothermal conditions in an herbal-decoction machine for about 2 hours.

1-5. Preparation of Extract of Cinnamomi Twigs and Moutan Root Bark (1:4) (CMO3)

An extract of Cinnamomi twigs and Moutan root bark (CMO3) was prepared in the same manner as in Example 1-1, except that 6 g of Cinnamomi twigs and 24 g of Moutan root bark were mixed at a ratio of 1:4, the mixture (30 g in total) was added to 180 mL of 50% ethanol, and the resultant was repeatedly extracted twice under reflux at about 50° C. for about 3 hours.

1-6. Preparation of Hydrothermal Extract of Cinnamomi Twigs and Moutan Root Bark (1:4) (CMO3-1)

A hydrothermal extract of Cinnamomi twigs and Moutan root bark (CMO3-1) was prepared in the same manner as in Example 1-2, except that 36 g of Cinnamomi twigs and 144 g of Moutan root bark were mixed at a ratio of 1:4, the mixture (180 g in total) was added to 1080 mL of purified water, and the resultant was extracted under hydrothermal conditions in an herbal-decoction machine for about 2 hours.

1-7. Preparation of Extract of Cinnamomi Twigs and Moutan Root Bark (1:8) (CMO4)

An extract of Cinnamomi twigs and Moutan root bark (CMO4) was prepared in the same manner as in Example 1-1, except that 3.5 g of Cinnamomi twigs and 28 g of Moutan root bark were mixed at a ratio of 1:8, the mixture (31.5 g in total) was added to 190 mL of 50% ethanol, and the resultant was repeatedly extracted twice under reflux at about 50° C. for about 3 hours.

1-8. Preparation of Hydrothermal Extract of Cinnamomi Twigs and Moutan Root Bark (1:8) (CMO4-1)

A hydrothermal extract of Cinnamomi twigs and Moutan root bark (CMO4-1) was prepared in the same manner as in Example 1-2, except that 20 g of Cinnamomi twigs and 160 g of Moutan root bark were mixed at a ratio of 1:8, the mixture (180 g in total) was added to 1080 mL of purified water, and the resultant was extracted under hydrothermal conditions in an herbal-decoction machine for about 2 hours.

Example 2. Comparison of Adipocyte Differentiation Inhibitory Effects of Mixed Extract of Cinnamomi Twigs and Moutan Root Bark (CMO1), Moutan Root Bark Extract, and Cinnamomi Twig Extract in Cell Lines 2-1. Comparison of Adipocyte Differentiation Inhibitory Effects of CMO1, Moutan Root Bark Extract, and Cinnamomi Twig Extract Adipocytes differentiated from 3T3-L1 were cultured in a 96-well plate for 4 days. The cultured adipocytes were treated with each of a mixed solution of IBMX, insulin, and dexamethasone (negative control), a mixed extract of Cinnamomi twigs and Moutan root bark (CMO1 10), a Moutan root bark extract (Moutan root bark 5), and a Cinnamomi twig extract (Cinnamomi twig 5) (Day 0). After 3 days, the insulin solution was replaced (Day 3). Thereafter, the cultivation was continued to Day 14 while replacing the insulin solution every 2 to 3 days.

In order to measure differentiation degrees of adipocytes, an Adipogenesis Assay Kit (Cayman chemical, Ann Arbor, Mich., USA) was used. The cells were immobilized and stained with an Oil Red 0 solution for about 20 minutes, and then Oil Red 0 was eluted using an extraction solution, followed by measuring absorbance at 492 nm.

2-2. Results of Experiment

As a result, while adipocyte differentiation was promoted 4-fold in the negative control, adipocyte differentiation was decreased by 56% compared to the negative control in the experimental group treated with the mixed extract of Cinnamomi twigs and Moutan root bark (CMO1), exhibiting excellent inhibitory effects. However, adipocyte differentiation was decreased by 41% and 10% in the experimental groups respectively treated with the extract of Moutan root bark alone and the extract of Cinnamomi twigs alone, which are components of the mixed extract of Cinnamomi twigs and Moutan root bark (CMO1). That is, the adipocyte differentiation inhibitory effects obtained by administration of CMO1 were enhanced by 46% compared to those obtained by administration of Cinnamomi twigs alone and by 15% compared those obtained by administration of Moutan root bark alone. Therefore, it may be confirmed that excellent synergistic effects are obtained by administering the mixed extract of Cinnamomi twigs and Moutan root bark compared to Cinnamomi twigs or Moutan root bark alone (FIG. 1).

Example 3. In Vivo Lipid Loading Test

The following experiment was conducted to analyze the ability of experimental animals to inhibit in vivo fat absorption.

3-1. Experimental Method 6-week-old male Sprague Dawley (SD) rats (DBL, Eumseong, Korea) were acclimated for one week and fasted for 16 hours. 6 mL of corn oil (Sigma, MO, USA), 80 mg of cholic acid (Sigma, MO, USA), 2 mg of cholesteryl oleate (Sigma, MO, USA), and 6 mL sterile saline (JW Choongwae Pharm, Korea) were mixed and sonicated to prepare a lipid emulsion. Subsequently, the mixed extract of Cinnamomi twigs and Moutan root bark (CMO1, 100 mg/kg), as a test drug, and Xenical™ (Orlistat, 10 mg/kg), as a positive control, were mixed. The drug was orally administered in a volume of 5 mL/kg, the negative control was administered with the same amount of sterile saline, and the positive control was administered with the same amount of the lipid emulsion not including the drug. At 30, 60, 120, and 180 minutes before and after administration of the test drug, blood was collected from caudal veins and centrifuged at 5000 rpm for 10 minutes to separate plasma, and the concentration of triacylglycerides (TG) in the blood was analyzed using a TG assay kit (Asan pharm, Korea).

An administration concentration of Xenical™ of about 12 mg/kg was calculated by applying a human equivalent dose conversion factor of 6.2, which was converted based on body surface area of rats from an administration concentration of 120 mg for an adult having a weight of 60 kg. In this test, 10 mg/kg of Xenical™ was administered to rats.

3-2. Results of Experiment

As shown in FIG. 2, in the oil emulsion-administered group, as the negative control, the concentration of triglycerides absorbed into the blood tended to increase up to 2 hours and slightly decrease thereafter. However, in the CMO1 mixture-administered group (250 mg/kg), lipid absorption was delayed, thereby inhibiting an increase in triglycerides in the blood. Analysis results of a total amount of triglycerides (TG AUC) in the blood for 3 hours also showed that an increase in the total amount of triglycerides was significantly inhibited in the mixture-administered group administered with a high concentration of CMO1. Via this test, it was confirmed that the CMO1 mixture inhibited an increase in triglycerides in the blood via a lipid absorption inhibition mechanism in the intestinal tract.

Example 4: Anti-Obesity Effect by Repeated Administration for 8 Weeks in Obesity Model Induced by High-Fat Diet 4-1. Experimental Method (1) Breeding of Experimental Animal and Design of Experiment 6-week-old male C57BL/6 mice (Orient Bio) were used after being acclimated for one week. A high-fat diet was fed to induce obesity. D12451 (Calorie composition: 45% of fats, 35% of carbohydrates, and 20% of proteins, Research Diets, Inc.) was used as the high-fat diet, and Purina Rodent Chow was used as a normal diet. The mice were allowed to freely access feed and drinking water. The CMO1 mixture was administered together with the D12541 feed at a weight ratio of 0.1% (w/w) and 0.25% (w/w). Xenical™ (orlistat, Sigma, MO, USA), as a control drug, was administered together with the D12541 feed in a weight ratio of 0.1% (w/w). A daily dose of the CMO1 mixture, calculated based on an average daily feed intake, was 70 mg/kg/day in the case of 0.1%, and 190 mg/kg/day in the case of 0.25%, and a daily dose of Xenical™ was 210 mg/kg/day. Body weights and feed intakes were measured every week, and organs were excised and weighed in autopsy after 8 weeks and then stored at −80° C.

(2) Blood Biochemical Analysis

In autopsy, blood was collected from the abdominal vein after laparotomy under deep anesthesia. The blood was stored in a cryogenic refrigerator according to analysis conditions and thawed immediately before initiating the experiment. Levels of total cholesterol, triglyceride, HDL cholesterol, and LDL cholesterol were analyzed using an automatic blood biochemistry analyzer (Hitachi, Japan).

(3) Measurement of Morphological Size Change of Adipocytes

In order to analyze size changes in adipocytes and hepatocytes caused by accumulation of fats, the organ was immobilized with 10% neutralized formalin (Microme, USA) for 24 hours, embedded into paraffin blocks via a general tissue treatment process, and sectioned into 4 μm slices. The slices were hydrated and stained with hematoxylin and eosin (H&E). The stained tissue was observed using an optical microscope (BX51, Olympus, Japan) to measure sizes of cells.

(4) Oil Red O Staining

In autopsy, liver tissue was collected, fixed in Bouin's solution including 20% sucrose, washed with phosphate buffered saline, dried, and immobilized in an optical cutting temperature compound (Finetek, CA, USA) as a cryostatic section embedding medium to prepare a cryostatic section block, and sectioned using a tissue sectioner. The liver tissue section was stained with Oil red O by a free floating method and observed using an optical microscope to obtain images thereof.

(5) Statistical Analysis

All measurement values of each experiment are expressed as mean±standard error. Statistical analysis was performed with Graph Pad Prism program ver 5.0 (GraphPad, CA, USA) using ANOVA test and Tukey Multiple Comparison test as post hoc analysis to measure significant difference. A P value less than 0.05 was regarded as statistically significant.

4-2. Results of Experiment

(1) Change in Body Weight

As a result of measuring changes in body weights for 8 weeks, the body weight of the high-fat diet-fed group continuously increased after 1 week compared to the normal diet-fed group, and the increase in body weight of the CMO1-administered group (0.25%) was significantly inhibited after 4 weeks compared to the high-fat diet-fed group.

(2) Feed Intake Change

No change was observed in feed intakes for 8 weeks in the CMO1-administered group (FIG. 4).

(3) Change in Abdominal Fat and Fat Weight

While weights of the epididymal fat, perirenal fat, and subcutaneous fat increased in the high-fat diet-fed group by 3- to 4-fold, increase in the weights were significantly inhibited in the CMO1-administered group (0.25%) (FIG. 5).

(4) Size of Adipocytes

While sizes of adipocytes increased in the high-fat diet-fed group by 1.6-fold or more, adipocyte hypertrophy due to fat accumulation was significantly inhibited in the CMO1-administered group (0.25%) (FIG. 6).

(5) Change in Lipid Content in Blood

While concentrations of total cholesterol, triglyceride, LDL cholesterol, and free fatty acid (FFA) considerably increased in the high-fat diet-fed group compared to the normal diet-fed group, and concentrations significantly decreased in the CMO1-administered group (0.25%) (FIG. 7).

(6) Change in Fatty Liver

A significant amount of fat is accumulated in liver tissue in the high-fat diet-fed group, and an area of lipid increased in hepatocytes based on Oil red O staining analysis. However, in the CMO1-administered group (0.25%), increased liver weight and the area of fat in hepatocytes were significantly decreased. Also, the amount of triglycerides (TG) in the liver tissue was also significantly reduced (FIG. 8).

(7) Verification of Diarrhea, Serious Side Effect of Xenical™

No diarrhea, which is a serious side effect of Xenical™, was observed in the CMO1-administered group. Hair of each group was observed during the administration. While the Xenical™-administered group had oily and lumpy hair as if the whole body was covered with oil due to diarrhea, hair of the other groups was normal. In autopsy, the same symptoms were identified when the mice were laid on their sides and on their backs after anesthesia. Also, as a result of comparing excrement, while the Xenical™-administered group showed very soft excrement, the other groups showed excrement with normal hardness. It was verified that the mixed extract overcame serious side effects of Xenical™ such as inhibition of fat-soluble vitamin absorption, gastric disturbance, and frequent diarrhea (FIG. 9).

Based on these results, it is confirmed that the mixed extract of Cinnamomi twigs and Moutan root bark has considerably excellent preventive or therapeutic effects on obesity, particularly as a safe therapeutic agent by overcoming serious side effects of conventional drugs such as Xenical™.

Descriptions of details apparent to those skilled in the art having ordinary knowledge in the technical field of the present invention or relevant fields thereof are omitted in the above descriptions, and various changes and modifications may be made without changing the technical conception and essential features of the present invention. Therefore, those skilled in the art will recognize that the present invention may be implemented in a manner different from that specifically discussed in the present application.

The invention claimed is:

1. A method of preventing or treating obesity, the method comprising administering a pharmaceutical composition consisting of a mixed extract of Cinnamomi twigs and Moutan root bark as an active ingredient to a person, wherein obesity is prevented or treated in the person,
   wherein the Cinnamomi twigs and Moutan root bark are mixed in a weight ratio of 1:1 to 1:8; and
   wherein the extract is obtained using water, ethanol, or any mixture thereof, as a solvent.

2. The method of claim 1, wherein the extract is obtained by hot-water extraction, reflux extraction, hydrothermal extraction, maceration extraction, room-temperature extraction, ultrasonication extraction, or steam extraction.

3. The method of claim 1, wherein the person is obese, and wherein the obesity is treated.

* * * * *